US010360650B2

(12) United States Patent
Harris et al.

(10) Patent No.: US 10,360,650 B2
(45) Date of Patent: Jul. 23, 2019

(54) SYSTEMS AND METHODS FOR REAL-TIME GROUP CODING (71) Applicant: 3M INNOVATIVE PROPERTIES COMPANY, St. Paul, MN (US)

(72) Inventors: Elizabeth Harris, Salt Lake City, UT (US); Christopher J. Hepworth, Centerville, UT (US); Jason M. Mark, Fruit Heights, UT (US); Jeramie P. Naef, Pasco, WA (US); Cindy R. Wilkey, Salt Lake City, UT (US)

(73) Assignee: 3M INNOVATION PROPERTIES COMPANY, St. Paul, MN (US)

( * ) Notice: Subject to any disclaimer, the term of this patent is extended or adjusted under 35 U.S.C. 154(b) by 390 days.

(21) Appl. No.: 14/133,685

(22) Filed: Dec. 19, 2013

(65) Prior Publication Data
US 2015/0178874 A1 Jun. 25, 2015

(51) Int. Cl.
*G16H 10/60* (2018.01)
*G06Q 50/24* (2012.01)
*G06Q 10/10* (2012.01)

(52) U.S. Cl.
CPC ............ *G06Q 50/24* (2013.01); *G06Q 10/10* (2013.01)

(58) Field of Classification Search
CPC .... G06F 19/322–328; G06Q 50/22–24; G06Q 10/10; G16H 10/60
See application file for complete search history.

(56) References Cited

U.S. PATENT DOCUMENTS

| 5,307,262 | A | 4/1994 | Ertel | |
| 6,915,254 | B1 * | 7/2005 | Heinze | G06F 17/27 382/225 |
| 7,624,027 | B1 | 11/2009 | Stern et al. | |
| 7,725,330 | B2 * | 5/2010 | Rao | G06F 19/328 705/2 |
| 2003/0154085 | A1 * | 8/2003 | Kelley | G06F 17/243 704/275 |
| 2010/0094649 | A1 * | 4/2010 | White | G06F 19/324 705/2 |
| 2010/0306135 | A1 | 12/2010 | McCallum et al. | |
| 2012/0078646 | A1 * | 3/2012 | Toleti | G06F 19/00 705/2 |
| 2012/0303383 | A1 | 11/2012 | Smith | |
| 2013/0073301 | A1 | 3/2013 | Rao | |

OTHER PUBLICATIONS

International Search Report for PCT International Application No. PCT/US2014/069022 dated Mar. 3, 2015, 2 pages.

\* cited by examiner

*Primary Examiner* — Sheetal R Paulson
(74) *Attorney, Agent, or Firm* — X. Christina Huang; Steven A. Bern (57) ABSTRACT

A computer-implemented method for real-time coding of medical group codes such as diagnosis and procedure related groups is described. In one embodiment, one or more initial medical group codes may be assigned to a patient record based on a first set of inputs. Upon assigning the one or more initial medical group codes, a coding summary of the one or more assigned medical group codes may be displayed. While displaying the coding summary, at least one input from a subsequent set of inputs may be received and updating one or more medical group codes in the patient record.

17 Claims, 10 Drawing Sheets

SYSTEMS AND METHODS FOR REAL-TIME GROUP CODING

BACKGROUND

The use of computer systems and computer-related technologies continues to increase at a rapid pace. This increased use of computer systems has influenced the advances made to computer-related technologies and has been accelerated by the expansion of computer networks, including the Internet. Indeed, computer systems have increasingly become an integral part of the business world and the activities of individual consumers. Computer systems may be used to carry out several business, industry, and academic endeavors.

Many businesses use one or more computer networks to communicate and share data between the various computers connected to the networks. The productivity and efficiency of employees often require human and computer interaction. As a result, users of computer technologies continue to demand an increase in the efficiency of these technologies. Improving the efficiency of computer technologies is desirable to anyone who uses and relies upon computers.

Computing systems may be used to enter information regarding a patient diagnosis in order to resolve a diagnosis related group (DRG) code and/or a procedure related group (PRG) code assigned to a patient record during a coding process. Currently, users wait until reaching the end of the coding process to fix problems that come about while entering coding information, to compute patient summaries, to determine the impact of coding changes during the coding process, and so forth. In some cases, a user may have to enter information under one code set and then enter the same information again for another code set in order to compare grouping results between various code sets. As a result, benefits may be realized by offering systems and methods for improving medical coding efficiency of a patient record.

SUMMARY

According to at least one embodiment, a computer-implemented method for real-time coding of medical group codes such as diagnosis related groups (DRGs) and procedure related groups (PRGs) is described. In one embodiment, one or more initial medical group codes may be assigned to a patient record based on a first set of inputs. Upon assigning the one or more initial medical group codes, a coding summary of the one or more assigned medical group codes may be displayed. While displaying the coding summary, at least one input from a subsequent set of inputs may be received and one or more medical group codes in the patient record may be updated in real-time.

In one embodiment, upon receiving an input from the subsequent set of inputs, the described systems and methods may determine whether the input from the subsequent set of inputs affects an aspect of the coding summary. Upon determining the input from the subsequent set of inputs causes an aspect of the coding summary to be affected, the affected aspect of the coding summary may be updated in real-time. The updated aspect of the coding summary may be displayed prior to updating the one or more medical group codes. In some cases, the affected aspect of the coding summary may include a reimbursement amount computed in association with the one or more initial medical group codes. In some cases, the affected aspect of the coding summary comprises a weight value (e.g., DRG weight, etc.) associated with the one or more initial medical group codes.

In some embodiments, upon receiving a request for a patient report, the requested patient report may be displayed prior to updating the one or more medical group codes. The one or more initial medical group codes may be assigned to the patient record under a first health care classification system. Prior to assigning the one or more medical group codes, at least one alternative medical group code may be determined under a second health care classification system as an alternative to at least one of the initial medical group codes. In some cases, the first health care classification system may include a first international classification of diseases (ICD) revision (e.g., ICD-9, ICD-10, ICD-11, etc.) and the second health care classification system may include a second ICD that is different from the first ICD. In some cases, prior to updating the subsequent one or more medical group codes, information related to the alternative medical group codes may be displayed in the coding summary adjacent to information related to the one or more initial medical group codes.

A computing device configured for real-time coding of medical group codes such as DRGs and PRGs is also described. The device may include a processor and memory in electronic communication with the processor. The memory may store instructions that may be executable by the processor to assign one or more initial medical group codes to the patient record based on a first set of inputs, upon assigning the one or more initial medical group codes, display a coding summary of assigned one or more medical group codes, and while displaying the coding summary, receive at least one input from a subsequent set of inputs and one or more medical group codes in the patient record may be updated in real-time.

A computer-program product for real-time coding of medical group codes such as DRGs and PRGs is also described. The computer-program product may include a non-transitory computer-readable medium that stores instructions. The instructions may be executable by the processor to assign one or more initial medical group codes to the patient record based on a first set of inputs, upon assigning the one or more initial medical group codes, display a coding summary of assigned one or more medical group codes, and while displaying the coding summary, receive at least one input from a subsequent set of inputs and one or more medical group codes in the patient record may be updated in real-time.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The systems and methods described herein relate to real-time coding of medical group codes such as diagnosis related groups (DRGs) and/or procedure related groups (PRGs). Specifically, the systems and methods described herein relate to improving the medical coding efficiency of a patient record.

There may be many types of medical group codes for which the systems and methods of the present disclosure may be generally applicable. The use of DRGs and/or PRGs herein is for illustrative purposes only, and may be replaced with other types of medical group codes.

DRGs are part of a system that health providers use to classify hospital cases into a diagnosis group. DRGs may be assigned by a grouper program based on the International Classification of Diseases (ICD) diagnoses and procedures. The classifications of groups may be based on patient information, including age, sex, discharge status, and the presence of complications or comorbidities. DRGs may be further grouped into Major Diagnostic Categories (MDCs). The fundamental principle of DRGs is that severity of illness and risk of mortality both depend on the patient's underlying condition. High severity of illness and risk of mortality are characterized by multiple serious diseases and the interactions between disorders. PRGs may be associated with a system that health providers user to classify procedures performed on a patient by hospital staff. Some examples of methodologies for grouping outpatient, ambulatory diagnosis, procedures, and/or encounters include, but are not limited to Ambulatory Payment Classification (APC) groups and Outpatient Prospective Payment Systems (OPPS), Ambulatory Payment Groups (APGs) and Ambulatory Surgical Centers (ASCs).

Healthcare providers generate volumes of patient information that result in coded medical records. This coded data is valuable to providers, regulators, payors, and consumers who want to understand the value of patient care. A careful analysis of an organization's coded data can provide insights into patient metrics, expected reimbursement, and quality outcomes. Inpatient and outpatient classification and grouping methodologies are used to help organizations review coded data and claims in order to validate codes, calculate payment based on payor rules and regulations, edit documentation, represent patient severity of illness (SOI) and risk of mortality (ROM), adjust and assign patient records to DRGs/PRGs, and track potentially preventable events, such as avoidable readmissions and hospital acquired conditions.

Benefits of the systems and methods described herein include allowing a user to fix coding issues while coding rather than waiting to the end of the coding process, real-time access to a patient summary at any stage of the coding process, eliminating the need to compute a patient summary at the end of the coding process, indicating the impact of coding changes during the coding process, alerting users to the interrelationships that exist between the quality of the documentation and the reimbursement, simultaneous comparison of the grouping results between ICD-9, ICD-10, ICD-11, and other similar code sets, eliminating the need of user to manually compute DRGs and/or PRGs at the end of a coding session, providing real-time access to grouping reports. Examples of grouping reports may include a "Session Report," "APR Assignment Report," and/or "110 Analysis Report," and so forth. A Session Report (e.g., 3M™ Session Report) is an example of a report that may include a final DRG/PRG summary, including DRG/PRG weights, proprietary information and calculations that comes from other programs (e.g., 3M™ solutions such as Clinical Analyzer or Advanced Analyzer results), estimated reimbursement, comparison of the DRG with and without the impact of Hospital Acquired Condition (HAC) rules (if applicable), details of diagnosis and procedure codes and its impact on the final results or reimbursement, using Medicare Severity—Diagnosis Related Group (MS-DRG), SOI, and ROM for the primary and secondary groupers on a patient record. An ICD Analysis Report (e.g., ICD-9 Analysis Report, ICD-10 Analysis Report, etc.) is an example of a report that may include a side-by-side comparison of the ICD-9 DRG and estimated reimbursement to the ICD-10 DRG and estimated reimbursement. Additionally, or alternatively, the ICD Analysis Report may also display the ICD codes (e.g., ICD-9 and ICD-10 codes), specifying an impact on the MS-DRG, Major Complications and Comorbidities (MCC), Complications and Comorbidities (CC) and Hospital Acquired Condition (HAC) markings. An All Patient Refined-Diagnosis Related Group (APR-DRG) Assignment Report (e.g., a 3M™ APR-DRG Assignment Report) is an example of a report that may include outlining each step in proprietary information and calculations that comes from other programs (e.g., additional 3M™ systems) for Severity of Illness (SOI) and Risk of Mortality (ROM) Subclass assignment process for APR-DRG software (e.g., 3M™ APR-DRG software). The Assignment Report allows a user to see an assignment process for a diagnoses coded on a patient record.

Figure 1:
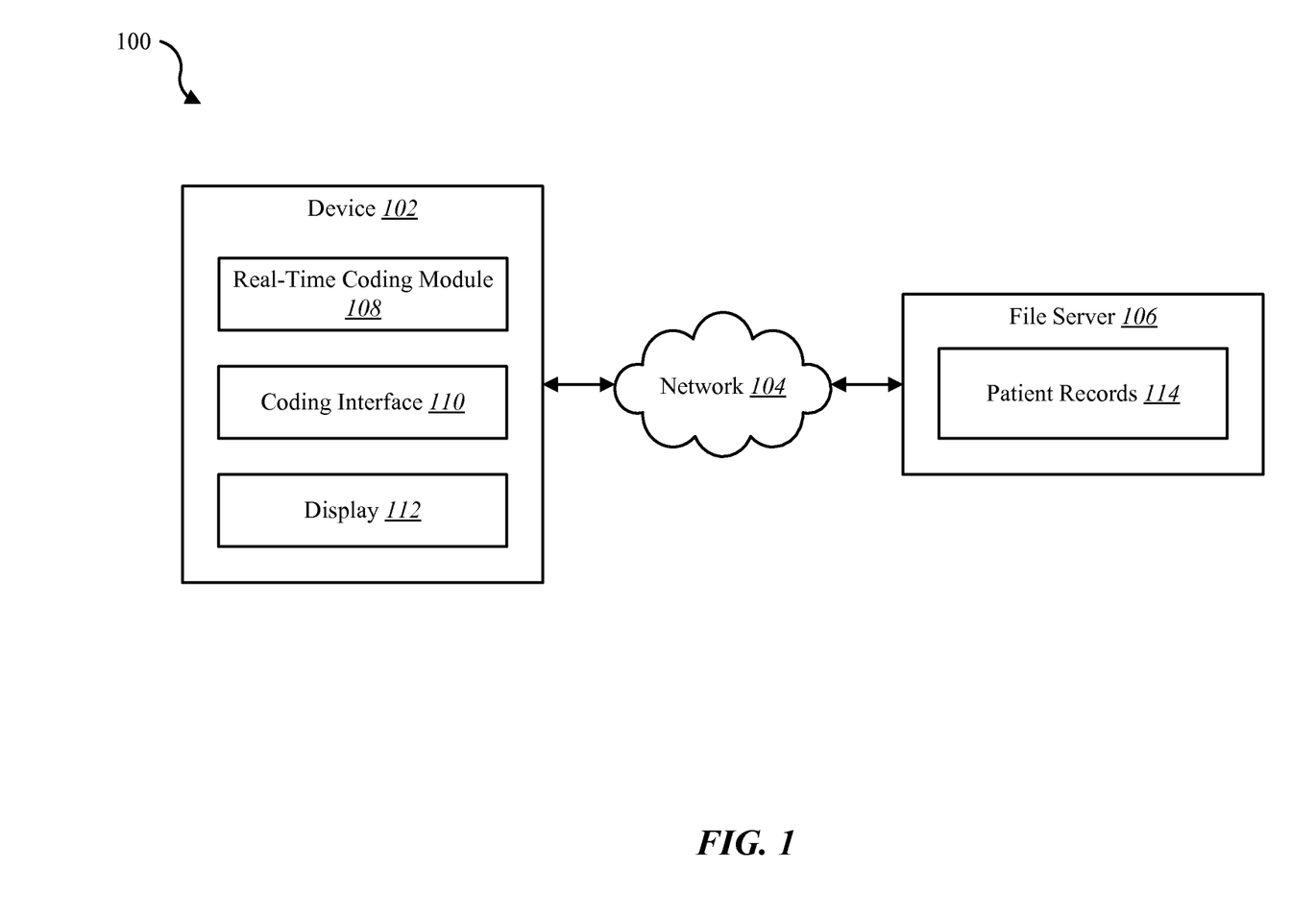
FIG. 1 is a block diagram illustrating one embodiment of an environment in which the present systems and methods may be implemented.

FIG. 1 is a block diagram illustrating one embodiment of an environment 100 in which the present systems and methods may be implemented. In some embodiments, the systems and methods described herein may be performed on a single device (e.g., device 102). For example, a real-time coding module 108 may be located on the device 102. Examples of device 102 include personal computing devices, computers, servers, mobile devices, smart phones, tablet computing devices, etc.

In some embodiments, a device 102 may communicate with a file server 106 via a network 104. Some example networks 104 include local area networks (LAN), wide area networks (WAN), virtual private networks (VPN), wireless networks (using 802.11, for example), cellular networks (using 3G and/or LTE, for example), cloud networks, one or more hosting environments, etc. In some configurations, the network 104 may include the Internet.

In some configurations, the device 102 may include a real-time coding module 108, a coding interface 110, and a display 112. In one example, the device 102 may be coupled to a file server 106. In some configurations, the file server 106 may serve patient records 114. The file server 106 may store the patient records 114 in a certain file structure. The coding interface 110 may allow a user to navigate the file structure in order to access the data.

In one embodiment, the real-time coding module 108 may provide a user with real-time grouping results, reimbursement information, and edits as a patient record is being coded. Real-time coding module 108 may present this information in a consolidated user interface, such as coding interface 110. Real-time coding module 108 may provide DRG and/or PRG information in real-time enabling a user to correct problems during the process of coding the patient record rather than after the record is coded. Real-time coding module 108 may improve a user's workflow by providing results in a timely manner, ensuring accuracy of hospital reimbursement, streamlining the user's workflow, and improving user productivity.

Figure 2:
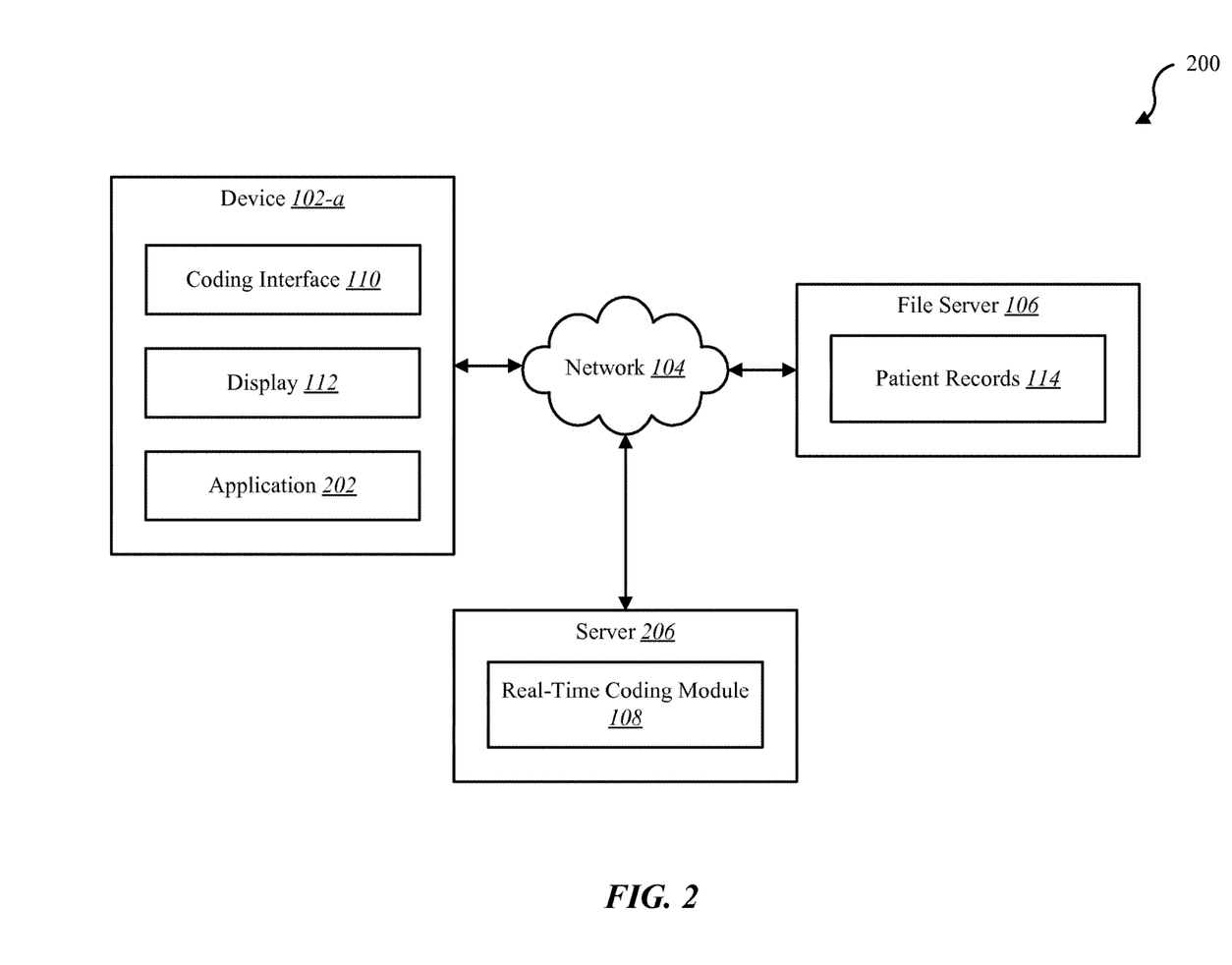
FIG. 2 is a block diagram illustrating another embodiment of an environment in which the present systems and methods may be implemented.

FIG. 2 is a block diagram illustrating another embodiment of an environment 200 in which the present systems and methods may be implemented. The environment 200 may include a device 102-a, a file server 106, and a server 206.

In some configurations, device 102-a may be one example of device 102 illustrated in FIG. 1. For example, the device 102-a may include the coding interface 110, the display 112, and an application 202. It is noted that in some embodiments, the device 102-a may not include a real-time coding module 108. In some embodiments, both the device 102-a and the server 206 may include the real-time coding module 108 where at least a portion of the functions of the real-time coding module 108 may be performed separately and/or concurrently on both the device 102-a and the server 206. The depicted file server 106 may include patient records 114.

In some embodiments, application 202 may operate in conjunction with the real-time coding module 108. In some configurations, the application 202 may allow interaction and/or handle communications between real-time coding module 108 located on server 206 and coding interface 110 located on device 102-a. Application 202 may include a web application. Further details of the real-time coding module 108 are described below.

Figure 3:
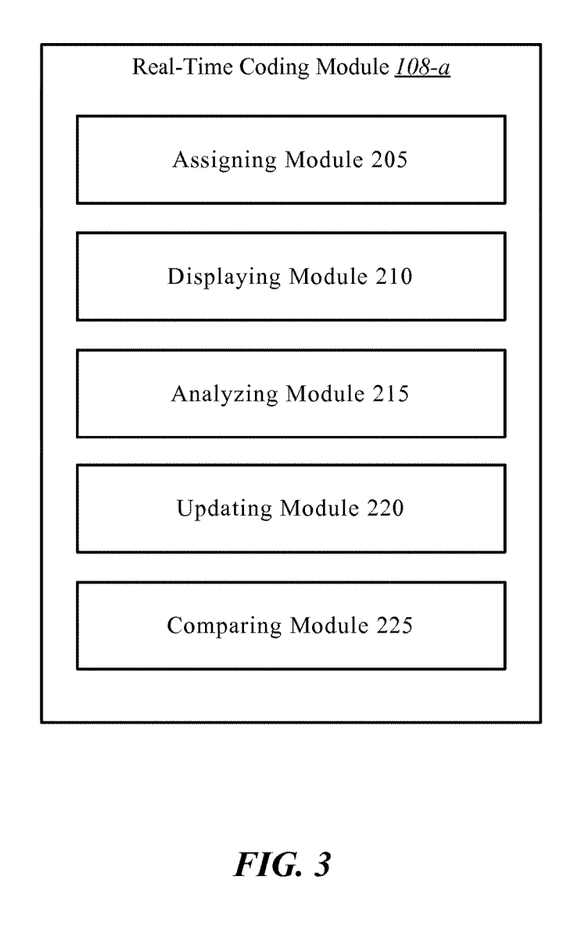
FIG. 3 is a block diagram illustrating one example of a navigating module.

FIG. 3 is a block diagram illustrating one example of a real-time coding module 108-a. The real-time coding module 108-a may be one example of the real-time coding module 108 depicted in FIGS. 1 and/or 2. As depicted, the real-time coding module 108-a may include assigning module 205, displaying module 210, analyzing module 215, updating module 220, and comparing module 225.

In one embodiment, the assigning module 205 may assign one or more initial medical group codes to the patient record based on a first set of inputs. Examples of medical group codes may include DRGs, PRGs, and any other type of coding formats for outpatient procedures, inpatient procedures, patient diagnoses, etc. For example, a user may enter information that the assigning module 205 uses to resolve one or more DRGs. In some cases, the assigning module 205 may present a list of options for the user to choose from based upon the information entered by the user. As an example, the user may enter the letters "CV" into a field. As a result, assigning module 205 may analyze the entered letters "CV" to determine a list of possible diagnoses the user intended to resolve by entering "CV." Displayed options may include "CVA (cerebrovascular accident) (embolic) (ischemic) (thrombotic)" as a first option, "CVA, hemorrhagic, non-traumatic" as a second option, and CVAgamma (common variable agammaglobulinemia)" as a third option. The assigning module 205 may prompt the user to select at least one of the displayed options. Upon receiving a selected option from the user, assigning module 205 may determine whether more information is needed to resolve the diagnosis code. Accordingly, assigning module 205 may request additional input and/or information from the user in order to assist the user in resolving the one or more initial medical group codes.

In some embodiments, upon assigning the one or more initial medical group codes, displaying module 210 may display a coding summary of the one or more assigned medical group codes. For example, displaying module 210 may display the one or more initial medical group codes via display 112. Displaying module 210 may display the coding summary in real-time upon resolving the one or more initial medical group codes. While displaying the coding summary of the one or more initial medical group codes, assigning module 205 may receive at least one input from a subsequent set of inputs and update one or more medical group codes in the patient record. For example, after receiving a first set of inputs that the assigning module 205 uses to assign one or more initial medical group codes, assigning module 205 may receive a subsequent set of inputs that a user enters in order to resolve one or more medical group codes, or medical group codes the assigning module 205 resolves and assigns after assigning the one or more initial medical group codes. While the assigning module 205 receives an input from the subsequent set of inputs, the displaying module 210 simultaneously displays the coding summary that includes the one or more resolved and assigned initial medical group codes.

In some embodiments, assigning module 205 may assign the one or more initial medical group codes to the patient record under a first health care classification system. In some cases, assigning module 205 may determine, prior to updating the one or more medical group codes, at least one alternative medical group code under a second health care classification system as an alternative to at least one of the initial medical group codes. For example, the first health care classification system may include international classification of diseases revision 9 (ICD-9). The second health care classification system may include an ICD different from the first health care classification. Additionally, or alternatively, assigning module 205 may determine one or more additional alternative medical group codes under one or more other health care classification systems in addition to or in place of ICD-9, ICD-10, ICD-11, and/or another similar coding classification. In some embodiments, prior to updating the subsequent one or more medical group codes, displaying module 210 may display in the coding summary information related to one or more alternative medical group codes adjacent to information related to the one or more initial medical group codes.

In some embodiments, upon receiving an input from the subsequent set of inputs, analyzing module 215 may determine whether an input from the subsequent set of inputs affects an aspect of the coding summary. As described above, the coding summary is displayed while the user enters the subsequent set of inputs. The coding summary may be updated in real-time while the user enters the subsequent set of inputs. As the user enters an input from the subsequent set of inputs, the analyzing module 215 may simultaneously analyze the effect the input from the subsequent set of inputs has on one or more aspects of the information contained in the coding summary being displayed (e.g., reimbursement, DRG/PRG weight, length of stay information, etc.) while the user enters the subsequent set of inputs.

Upon determining the input from the subsequent set of inputs causes an aspect of the coding summary to be affected, the updating module 220 may update the affected aspect of the coding summary in real-time. Accordingly, displaying module 210 may display the updated aspect of the coding summary in real-time. In one embodiment, displaying module 210 may display the updated aspect of the coding summary and update the one or more medical group codes. In some cases, the affected aspect of the coding summary may include a reimbursement amount computed in association with the one or more initial medical group codes. In some embodiments, the affected aspect of the coding summary may include a DRG/PRG weight associated with the one or more initial medical group codes. Accordingly, while the user enters one or more inputs from the subsequent set of inputs, the displaying module 210 may display a reimbursement amount in the coding summary. The displayed amount may be a first amount, such as $4,200.00, as an example.

Upon receiving an input from the subsequent set of inputs, the analyzing module 215 may determine that the received input from the subsequent set of inputs affects the reimbursement amount. For example, the analyzing module 215 may determine that the reimbursement amount is adjusted to $6,800.00 based on the received input from the subsequent set of inputs. Updating module 220 may update the reimbursement amount to $6,800.00. Upon detecting the updating of the reimbursement amount, the displaying module 210 may display the updated amount in the coding summary, adjusting the first amount of $4,200.00 to the updated amount of $6,800.00 while the user enters one or more inputs of the subsequent set of inputs. Thus, the displaying module 210, in conjunction with the analyzing module 215 and/or updating module 220, may display an updated aspect of the coding summary in real-time while the user enters one or more inputs from a subsequent set of inputs.

In one embodiment, upon receiving a request for a patient report, displaying module 210 may display the requested patient report and update the one or more medical group codes. For example, after entering a first set of inputs the coding summary may include one or more assigned DRGs and/or PRGs that are displayed to the user. Before resolving and assigning one or more medical group codes, the user may request a patient report. The patient report may contain information regarding the patient including information entered by the user, information regarding the assigned medical group codes, information from a patient profile, information from a patient history including previous procedures, and the like. Accordingly, without interruption to the coding pathway that the user may be currently navigating in relation to the subsequent set of inputs, the displaying module 210 may simultaneously display a requested patient report while the user enters one or more inputs from the subsequent set of inputs.

Figure 4:
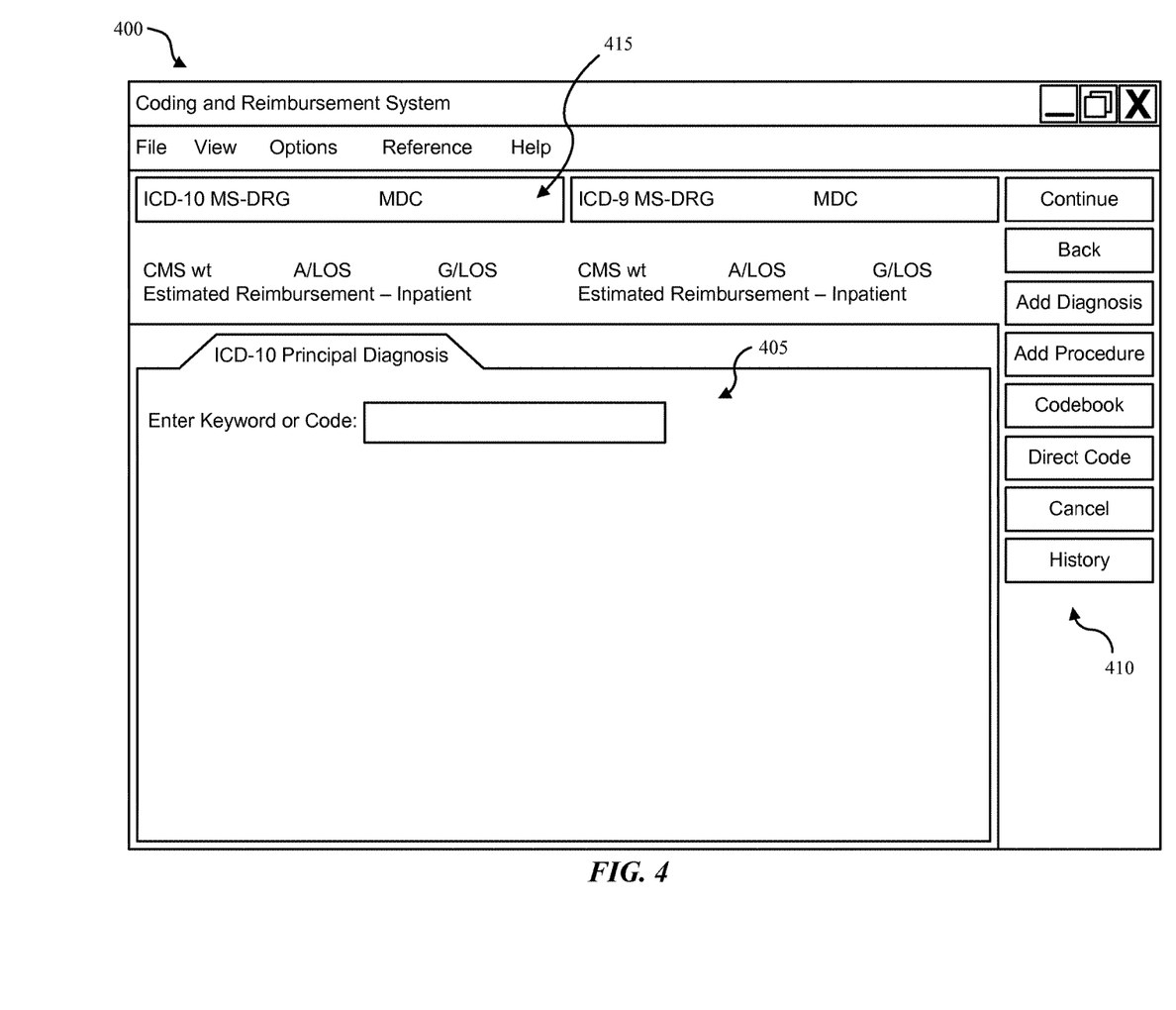
FIG. 4 illustrates an example arrangement of a user interface.

FIG. 4 illustrates an example arrangement of a user interface 400. User interface 400 may be one example of coding interface 110 of FIGS. 1 and/or 2. The user interface 400 may include an entry field 405, user controls 410, and a coding summary 415.

In one embodiment, entry field 405 may allow a user to enter diagnosis and/or procedure information relative to assigning one or more DRGs and/or PRGs. For example, entry field 405 may allow a user to enter a first set of inputs from which one or more initial medical group codes are resolved and assigned. Entry field 405 may allow a user to enter a second set of inputs from which one or more second DRGs and/or PRGs are resolved and assigned. As a user enters information, one or more medical group codes may be updated in real-time, while the user is entering information. The user may control aspects of the user interface 400 via the user controls 410. For example, user controls 410 may allow a user to continue with a coding process, to add a diagnosis, add a procedure, and so forth. The coding summary 415 may include information related to one or more assigned DRGs and/or PRGs. For example, the coding summary 415 may include reimbursement information, DRG/PRG weight information, length of stay information, and the like. As described above, real-time coding module 108 may assign one or more initial medical group codes to a patient record based on a first set of inputs (e.g., entered via entry field 405). Upon assigning the one or more initial medical group codes, real-time coding module 108 may display information of the one or more assigned medical group codes in the coding summary 415. While displaying the information of the one or more assigned medical group codes in the coding summary 415, real-time coding module 108 may receive at least one input from a subsequent set of inputs that are received and analyzed by the real-time coding module 108 prior to the real-time coding module 108 assigning one or more medical group codes in the patient record.

Figure 5:
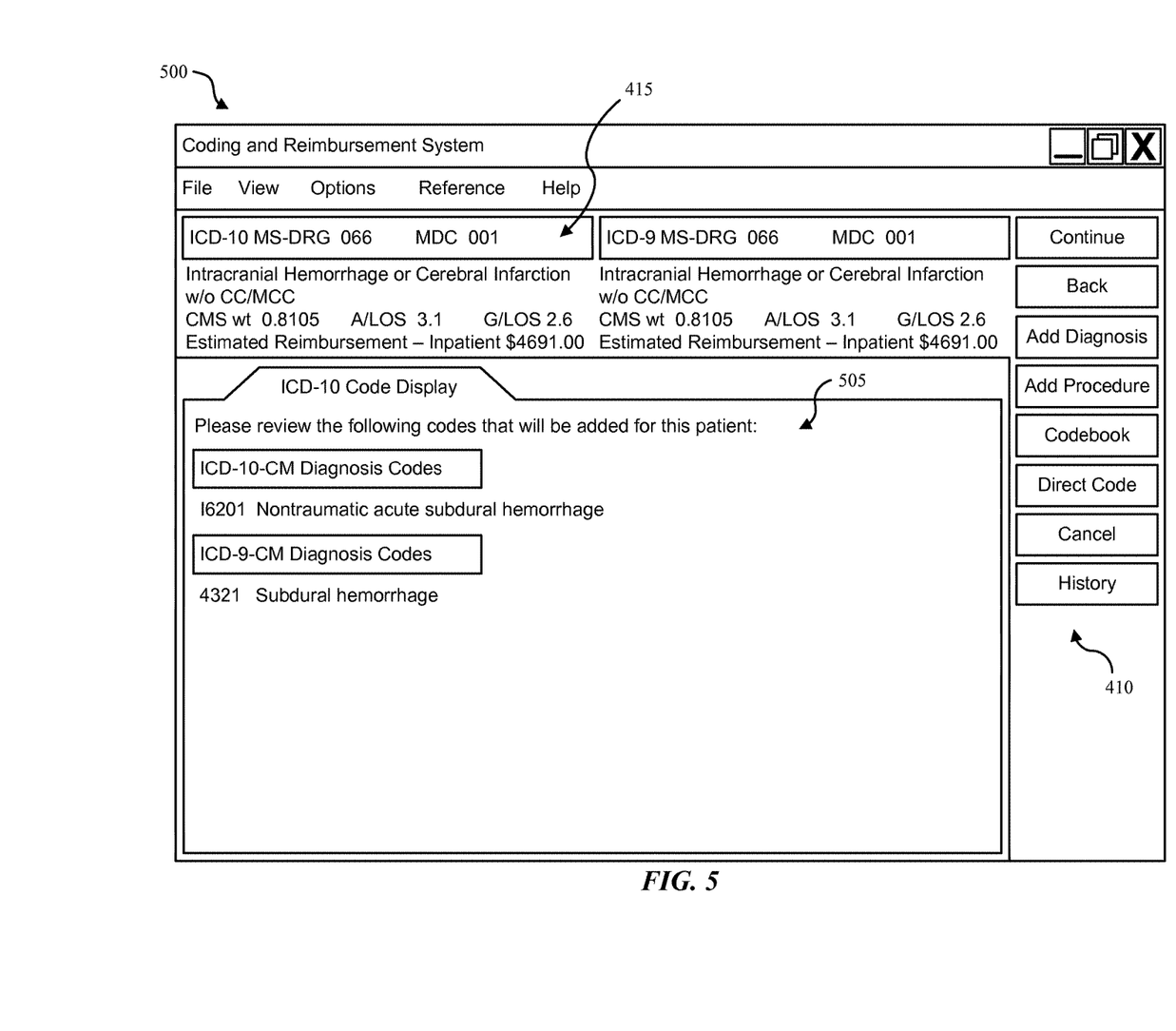
FIG. 5 illustrates another example arrangement of a user interface.

FIG. 5 illustrates another example arrangement of a user interface 500. User interface 500 may be one example of coding interface 110 of FIGS. 1 and/or 2, or one example of user interface 400 depicted in FIG. 4. As depicted, user interface 500 may include user controls 410, coding summary 415, and a code display 505.

In one embodiment, the code display 505 may include a list of one or more resolved medical group codes based on inputs entered by a user. The code display 505 may allow a user to review the resolved diagnosis codes before assigning the codes to a patient record. The user interface 500 may permit the user to add the resolved diagnosis codes via the user controls 410. Upon assigning the resolved diagnosis codes, real-time coding module 108 may update information in the coding summary 415 in real-time. As depicted, the coding summary 415 may include information related to one or more previously assigned medical group codes. Real-time coding module 108 may display in the coding summary 415 medical group code information based on a first health care classification system adjacent to alternative medical group code information based on a second health care classification system. Thus, real-time coding module 108 may offer a comparative view between two or more health care classification systems at any stage during the coding process. As depicted, the first health care classification system may include information based on the international classification of diseases revision 9 (ICD-9), ICD-10, ICD-11, and the like. The second health care classification system may include information based on an ICD different from the first health care classification. While the user enters information related to the resolved diagnosis codes, real-time coding module 108 may display information regarding the previously assigned medical group codes in the coding summary 415.

Figure 6:
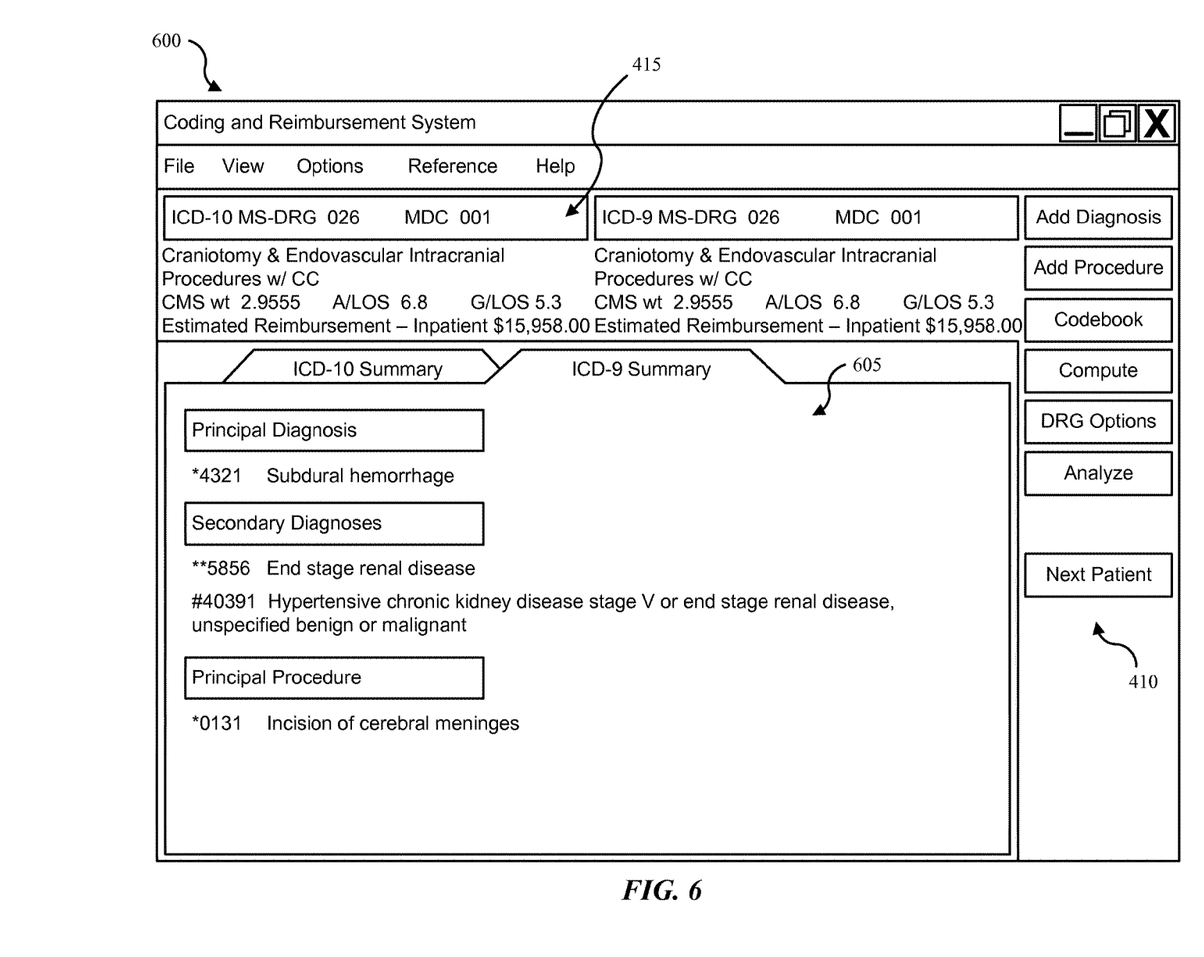
FIG. 6 illustrates another example arrangement of a user interface.

FIG. 6 illustrates another example arrangement of a user interface 600. User interface 600 may be one example of coding interface 110 of FIGS. 1 and/or 2, one example of user interface 400 depicted in FIG. 4, or one example of user interface 500 depicted in FIG. 5.

As depicted, user interface 600 may include user controls 410, coding summary 415, and a diagnosis and procedure summary 605. As depicted, the diagnosis and procedure summary 605 may include one or more tabs. For example, the diagnosis and procedure summary 605 may include a first tab for a summary of the resolved diagnosis and procedure codes under ICD-9, and may include a second tab for a summary of the resolved diagnosis and procedure codes under ICD-10. Additionally, or alternatively, one or more other ICD classifications may be used. As depicted, the coding summary 415 may include real-time updates based on inputs received. Accordingly, real-time coding module 108 may update, in the coding summary 415, information related to reimbursement amounts, DRG/PRG weights, length of stay information, and the like, in real-time as a user enters information related to the assignment of medical group codes.

Figure 7:
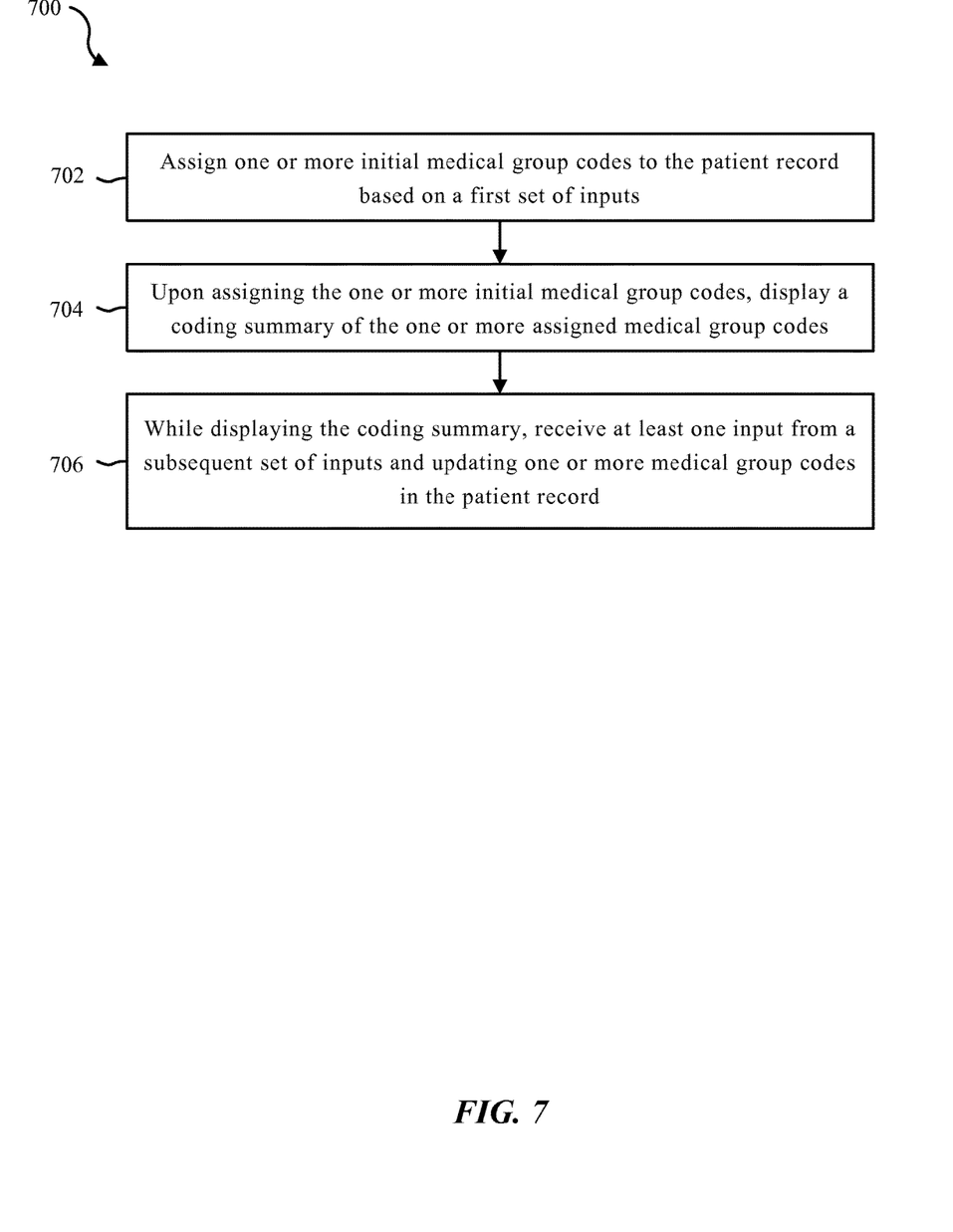
FIG. 7 is a flow diagram illustrating one embodiment of a method for simultaneously displaying one or more assigned medical group codes (e.g., DRGs and/or PRGs) based on a first set of inputs while receiving one or more inputs from a second set of inputs used to assigned one or more medical group codes.

FIG. 7 is a flow diagram illustrating one embodiment of a method 700 for simultaneously displaying one or more assigned medical group codes (e.g., DRGs and/or PRGs) based on a first set of inputs while receiving one or more inputs from a second set of inputs used to assigned one or more medical group codes. In some configurations, the method 700 may be implemented by the real-time coding module 108 illustrated in FIGS. 1, 2, and/or 3. In some configurations, the method 700 may be implemented by the application 202 illustrated in FIG. 2.

At block 702, one or more initial medical group codes may be assigned to a patient record based on a first set of inputs. At block 704, upon assigning the one or more initial medical group codes, a coding summary of the one or more assigned medical group codes may be displayed. At block 706, while displaying the coding summary, at least one input may be received from a subsequent set of inputs and one or more medical group codes may be updated to the patient record.

Figure 8:
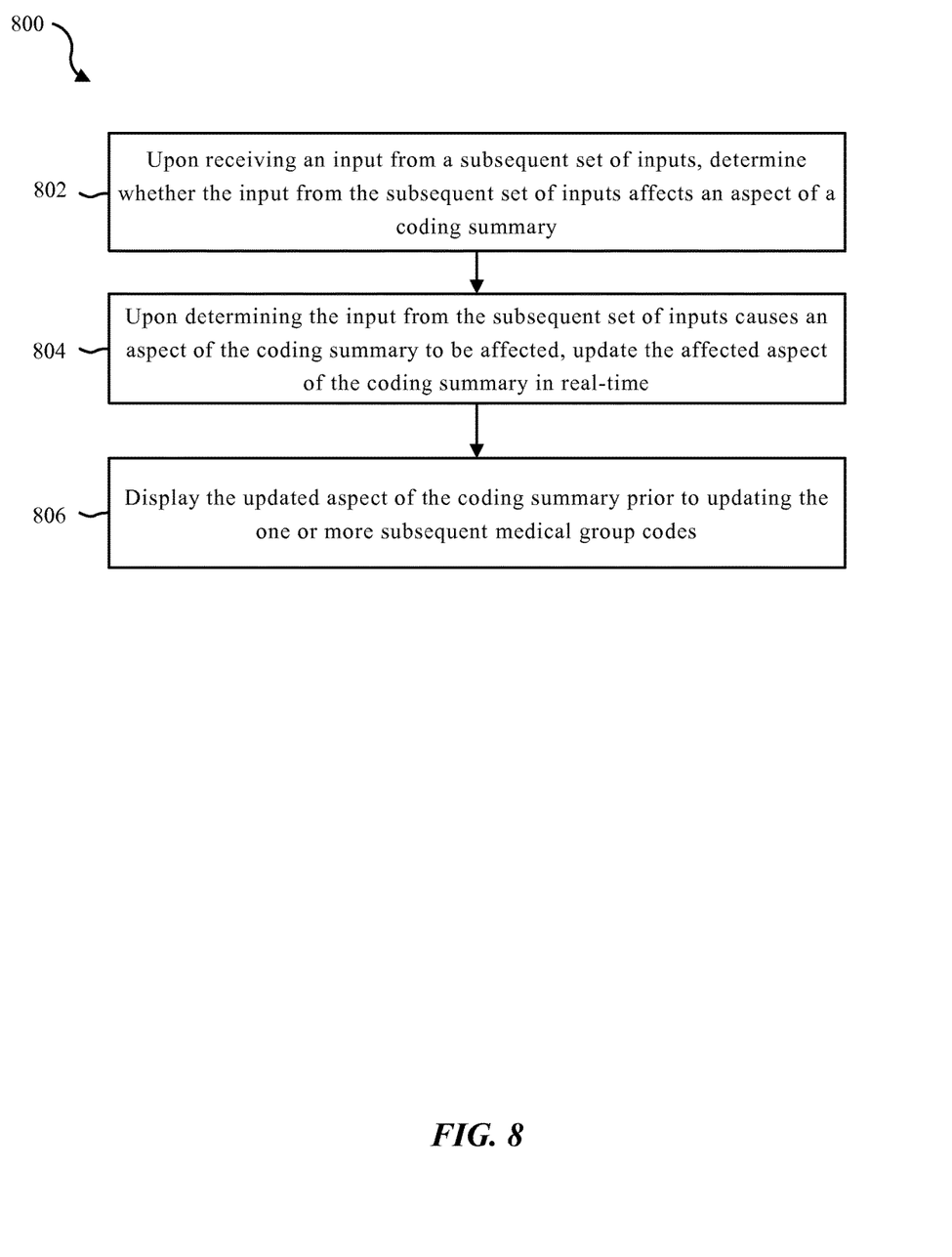
FIG. 8 is a flow diagram illustrating one embodiment of a method for updating an aspect of a coding summary in real-time while a user enters one or more inputs from a subsequent set of inputs used to derive one or more medical group codes.

FIG. 8 is a flow diagram illustrating one embodiment of a method 800 for updating an aspect of a coding summary in real-time while a user enters one or more inputs from a subsequent set of inputs used to derive one or more medical group codes. In some configurations, the method 800 may be implemented by the real-time coding module 108 illustrated in FIGS. 1, 2, and/or 3. In some configurations, the method 800 may be implemented by the application 202 illustrated in FIG. 2.

As described above, one or more initial medical group codes may be assigned to a patient record based on a first set of inputs, and upon assigning the one or more initial medical group codes, a coding summary of the one or more assigned medical group codes may be displayed. While displaying the coding summary, at least one input may be received from a subsequent set of inputs and one or more medical group codes may be updated to the patient record in real-time. At block 802, upon receiving an input from a subsequent set of inputs, it may be determined whether the input from the subsequent set of inputs affects an aspect of the coding summary. At block 804, upon determining the input from the subsequent set of inputs causes an aspect of the coding summary to be affected, the affected aspect of the coding summary may be updated in real-time. At block 806, the updated aspect of the coding summary may be displayed and the one or more medical group codes may be updated. The affected aspect of the coding summary may include a reimbursement amount and/or a DRG/PRG weight computed in association with the one or more initial medical group codes.

Figure 9:
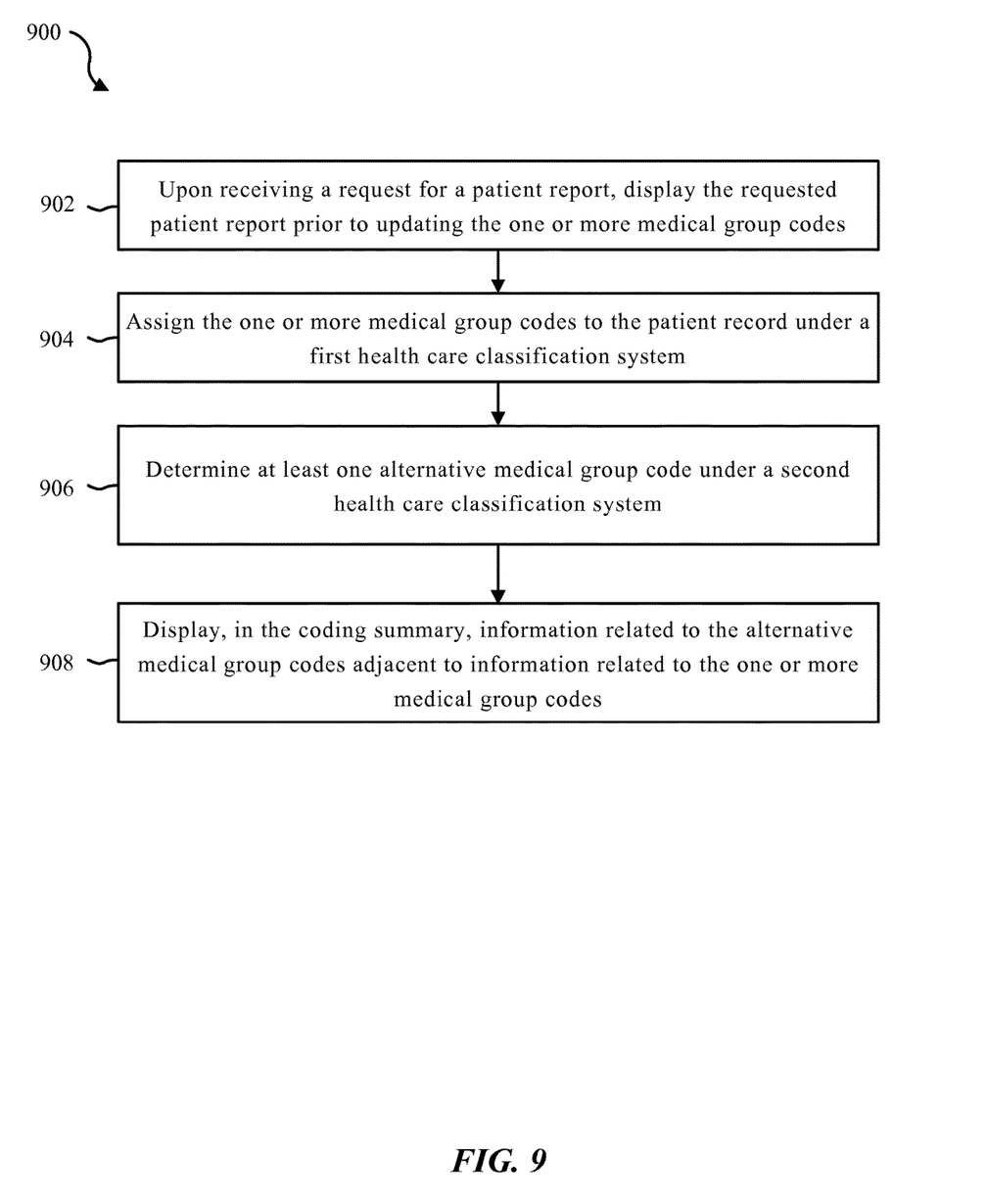
FIG. 9 is a flow diagram illustrating one embodiment of a method for determining, prior to updating one or more medical group codes, at least one alternative medical group code under a second health care classification system as an alternative to at least one of the initial medical group codes.

FIG. 9 is a flow diagram illustrating one embodiment of a method 900 for determining, prior to updating one or more medical group codes, at least one alternative medical group code under a second health care classification system as an alternative to at least one of the initial medical group codes. In some configurations, the method 900 may be implemented by the real-time coding module 108 illustrated in FIGS. 1, 2, and/or 3. In some configurations, the method 900 may be implemented by the application 202 illustrated in FIG. 2.

At block 902, after assigning and displaying one or more medical group codes and upon receiving a request for a patient report, a requested patient report may be displayed and/or one or more medical group codes may be updated. At block 904, the one or more medical group codes may be assigned to the patient record under a first health care classification system. At block 906 at least one alternative medical group code may be determined under a second health care classification system as an alternative to at least one of the assigned medical group codes. At block 908, in the coding summary, information related to the alternative medical group codes assigned under the second health care classification system may be displayed adjacent to information related to the one or more medical group codes assigned under the first health care classification system. The first health care classification system may include international classification of diseases revision 9 (ICD-9), ICD-10, ICD-11, or another similar ICD classification. The second health care classification system may include an ICD classification different from the first health care classification system.

Figure 10:
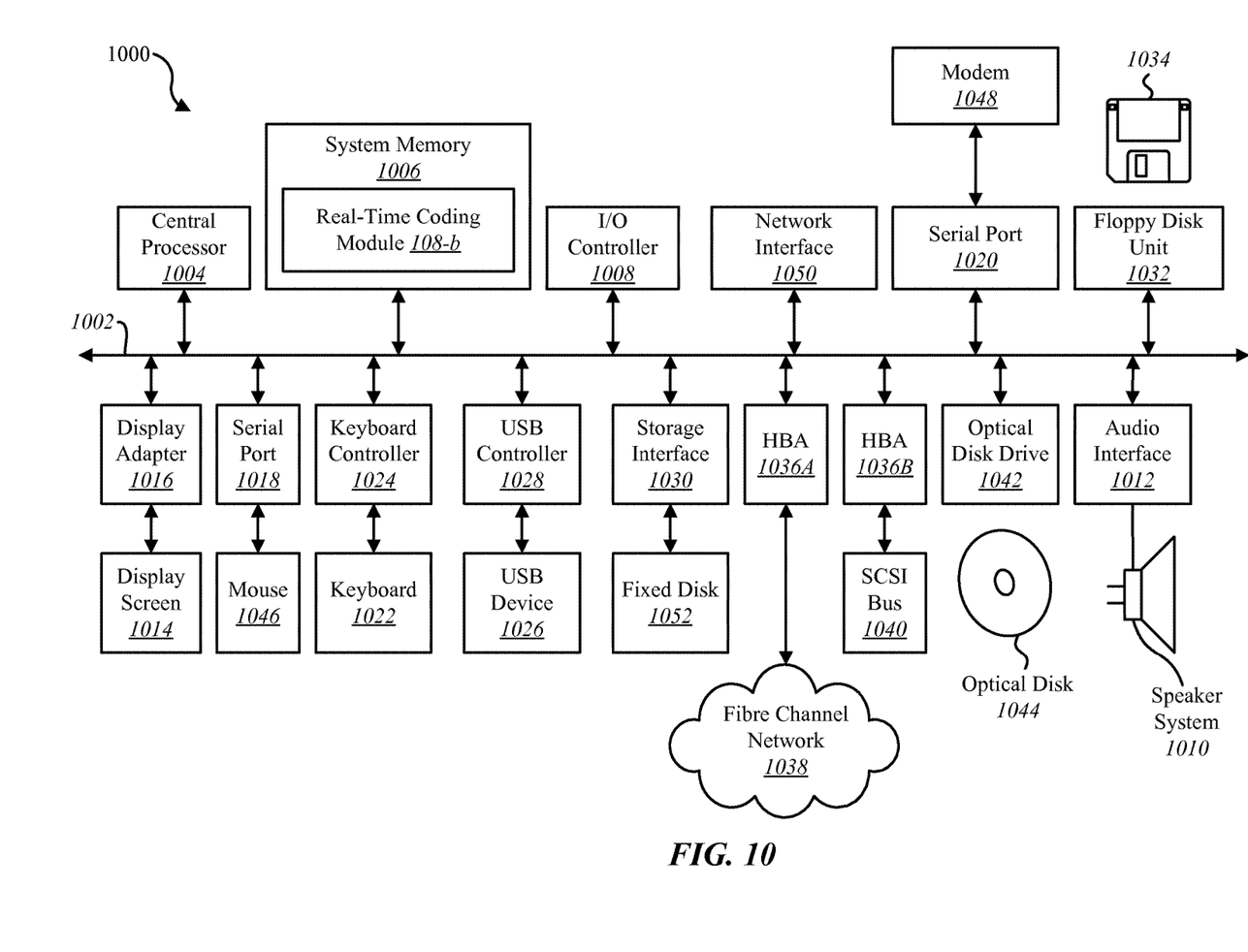
FIG. 10 depicts a block diagram of a computer system suitable for implementing the present systems and methods.

FIG. 10 depicts a block diagram of a computer system 1000 suitable for implementing the present systems and methods. The depicted computer system 1000 may be one example of a server 206 depicted in FIG. 2. Alternatively, the system 1000 may be one example of a device 102 depicted in FIGS. 1 and/or 2. Computer system 1000 includes a bus 1002 which interconnects major subsystems of computer system 1000, such as a central processor 1004, a system memory 1006 (typically RAM, but which may also include ROM, flash RAM, or the like), an input/output controller 1008, an external audio device, such as a speaker system 1010 via an audio output interface 1012, an external device, such as a display screen 1014 via display adapter 1016 (display screen 1014 including touch screens), serial ports 1018 and mouse 1046, a keyboard 1022 (interfaced with a keyboard controller 1024), multiple USB devices 1026 (interfaced with a USB controller 1028), a storage interface 1030, a host bus adapter (HBA) interface card 1036A operative to connect with a Fibre Channel network 1038, a host bus adapter (HBA) interface card 1036B operative to connect to a SCSI bus 1040, and an optical disk drive 1042 operative to receive an optical disk 1044. Also included are a mouse 1046 (or other point-and-click device, coupled to bus 1002 via serial port 1018), a modem 1048

(coupled to bus 1002 via serial port 1020), and a network interface 1050 (coupled directly to bus 1002). In some embodiments, computer system 1000 may connect to one or more devices via a network connection (e.g., via network interface 1050). In some cases, computer system 1000 connects to a cloud network via network interface 1050.

Bus 1002 allows data communication between central processor 1004 and system memory 1006, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, a real-time coding module 108-b to implement the present systems and methods may be stored within the system memory 1006. The real-time coding module 108-b may be one example of the real-time coding module 108 depicted in FIGS. 1, 2, and/or 3. Applications resident with computer system 1000 are generally stored on and accessed via a non-transitory computer readable medium, such as a hard disk drive (e.g., fixed disk 1052), an optical drive (e.g., optical drive 1042), or other storage medium. Additionally, applications can be in the form of electronic signals modulated in accordance with the application and data communication technology when accessed via network modem 1048 or interface 1050.

Storage interface 1030, as with the other storage interfaces of computer system 1000, can connect to a standard computer readable medium for storage and/or retrieval of information, such as a fixed disk drive 1052. Fixed disk drive 1052 may be a part of computer system 1000 or may be separate and accessed through other interface systems. Modem 1048 may provide a direct connection to a remote server via a telephone link or to the Internet via an internet service provider (ISP). Network interface 1050 may provide a direct connection to a remote server via a direct network link to the Internet via a POP (point of presence). Network interface 1050 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 10 need not be present to practice the present systems and methods. The devices and subsystems can be interconnected in different ways from that shown in FIG. 10. The operation of at least some of the computer system 1000 such as that shown in FIG. 10 is readily known in the art and is not discussed in detail in this application. Code to implement the present disclosure can be stored in a non-transitory computer-readable medium such as one or more of system memory 1006, fixed disk 1052, or optical disk 1044. The operating system provided on computer system 1000 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on"

as used in the specification and the claims is to be construed as meaning "based at least upon."

What is claimed is:

1. A computer-implemented method for improving medical coding efficiency of a patient record, the method comprising:

assigning, by an assigning module executed by a processor and during a coding process for the patient record, one or more initial medical group codes to the patient record in real-time based on a first set of inputs received from a user during the coding process;

upon assigning the one or more initial medical group codes, displaying, by a displaying module executed by the processor that controls a user interface, a coding summary of the one or more initial medical group codes as the patient record is being coded;

while displaying the coding summary:

receiving, by the processor and via the user interface during the coding process, at least one input from a subsequent set of inputs;

upon receiving the at least one input from the subsequent set of inputs, determining, by an analyzing module executed by the processor, whether the at least one input from the subsequent set of inputs affects an aspect of the coding summary;

upon determining the at least one input from the subsequent set of inputs causes the aspect of the coding summary to be affected, updating, by an updating module executed by the processor and in real-time, the affected aspect of the coding summary and the one or more initial medical group codes assigned in the patient record;

upon receiving the at least one input from the subsequent set of inputs, determining, by the analyzing module executed by the processor, whether additional information is needed to resolve another medical group code;

upon determining that the additional information is needed to resolve the another medical group code, requesting, by the analyzing module executed by the processor, additional user input to resolve the another medical group code;

upon receiving the additional user input, resolving, by the analyzing module executed by the processor, the another medical group code, wherein the updated aspect of the coding summary reflects the resolved another medical group code; and displaying, by the displaying module executed by the processor that controls the user interface, the updated affected aspect of the coding summary.

2. The method of claim 1, wherein the affected aspect of the coding summary comprises a reimbursement amount computed in association with the one or more initial medical group codes.

3. The method of claim 1, wherein the affected aspect of the coding summary comprises a medical group code weight associated with the one or more initial medical group codes.

4. The method of claim 1, further comprising:

upon receiving a request for a patient report, displaying the requested patient report prior to updating the one or more medical group codes.

5. The method of claim 1, further comprising:

assigning the one or more initial medical group codes to the patient record under a first health care classification system; and determining, prior to updating the one or more medical group codes, at least one alternative medical group code under a second health care classification system as an alternative to at least one of the initial medical group codes.

6. The method of claim 5, further comprising:

displaying, in the coding summary, prior to updating the one or more initial medical group codes, information related to the alternative medical group codes adjacent to information related to the one or more initial medical group codes.

7. The method of claim 5, wherein the first health care classification system comprises a first international classification of diseases (ICD) revision and the second health care classification system comprises a second ICD revision different from the first ICD.

8. A computing system configured to improve medical coding efficiency of a patient record, comprising:

a processor;

a memory in electronic communication with the processor; and instructions stored in the memory, the instructions comprising an assigning module, a displaying module, an analyzing module, and an updating module, the instructions being executable by the processor to:

assign, via the assignment module, during a coding process for the patient record, one or more initial medical group codes to the patient record in real-time based on a first set of inputs received from a user during the coding process;

upon assigning the one or more initial medical group codes, display, via the displaying module that controls a user interface, a coding summary of one or more initial medical group codes as the patient record is being coded;

while displaying the coding summary;

receive, via the user interface during the coding process, at least one input from a subsequent set of inputs;

upon receiving the at least one input from the subsequent set of inputs, determine, by the analyzing module, whether the at least one input from the subsequent set of inputs affects an aspect of the coding summary;

upon determining the at least one input from the subsequent set of inputs causes the aspect of the coding summary to be affected, update, by the updating module and in real-time, the affected aspect of the coding summary and the one or more initial medical group codes assigned in the patient record;

upon receiving the at least one input from the subsequent set of inputs, determine, by the analyzing module, whether additional information is needed to resolve another medical group code;

upon determining that the additional information is needed to resolve the another medical group code, request, by the analyzing module, additional user input to resolve the another medical group code;

upon receiving the additional user input, resolve, by the analyzing module, the another medical group code, wherein the updated aspect of the coding summary reflects the resolved another medical group code; and display, via the displaying module that controls the user interface, the updated affected aspect of the coding summary.

9. The computing system of claim 8, wherein the affected aspect of the coding summary comprises a reimbursement amount computed in association with the one or more initial medical group codes.

10. The computing system of claim 8, wherein the affected aspect of the coding summary comprises a medical group code weight associated with the one or more initial medical group codes.

11. The computing system of claim 8, wherein the instructions are executable by the processor to:
upon receiving a request for a patient report, display the requested patient report prior to updating the one or more medical group codes.

12. The computing system of claim 8, wherein the instructions are executable by the processor to:
assign the one or more initial medical group codes to the patient record under a first health care classification system; and
determine, prior to updating the one or more medical group codes, at least one alternative medical group code under a second health care classification system as an alternative to at least one of the initial medical group codes.

13. The computing system of claim 12, wherein the instructions are executable by the processor to:
display, in the coding summary, prior to updating the one or more initial medical group codes, information related to the alternative medical group codes adjacent to information related to the one or more initial medical group codes.

14. The computing system of claim 12, wherein the first health care classification system comprises a first international classification of diseases (ICD) revision and the second health care classification system comprises a second ICD revision different from the first ICD.

15. A computer-program product for improving, by a processor, medical coding efficiency of a patient record, the computer-program product comprising a non-transitory computer-readable medium storing instructions thereon, the instructions being executable by the processor to:
assign, by an assigning module executable by the processor and during a coding process for the patient record, one or more initial medical group codes to the patient record under a first health care classification system in real-time based on a first set of inputs received from a user during the coding process;
upon assigning the one or more initial medical group codes, display, by a displaying module executed by the processor that controls a user interface, a coding summary of one or more initial medical group codes as the patient record is being coded; determine, by the assigning module, at least one alternative medical group code under a second health care classification system as an alternative to at least one of the initial medical group codes;
display, by the displaying module, the at least one alternative medical group code under the second health care classification system;
while displaying the coding summary:
receive, via the user interface during the coding process, at least one input from a subsequent set of inputs;
upon receiving the at least one input from the subsequent set of inputs, determine, by an analyzing module executed by the processor, whether the at least one input from the subsequent set of inputs affects an aspect of the coding summary;
upon determining the at least one input from the subsequent set of inputs causes the aspect of the coding summary to be affected, update, by an updating module executed by the processor and in real-time, the affected aspect of the coding summary and the one or more initial medical group codes in the patient record;
upon receiving the at least one input from the subsequent set of inputs, determine, by the analyzing module executed by the processor, whether additional information is needed to resolve another medical group code;
upon determining that the additional information is needed to resolve the another medical group code, request, by the analyzing module executed by the processor, additional user input to resolve the another medical group code;
upon receiving the additional user input, resolve, by the analyzing module executed by the processor, the another medical group code, wherein the updated aspect of the coding summary reflects the resolved another medical group code; and
display, by the displaying module executed by the processor that controls the user interface, the updated affected aspect of the coding summary.

16. The computer-program product of claim 15, wherein the instructions being executable by the processor to display, by the displaying module, the at least one alternative medical group code under the second health care classification system comprises instructions being executable by the processor to, prior to updating the one or more medical group codes, display, by the displaying module and in the coding summary, information related to the at least one alternative medical group codes adjacent to information related to the one or more initial medical group codes.

17. The computer-program product of claim 15, wherein the first health care classification system comprises a first international classification of diseases (ICD) revision and the second health care classification system comprises a second ICD revision different from the first ICD.

* * * * *

UNITED STATES PATENT AND TRADEMARK OFFICE
CERTIFICATE OF CORRECTION

PATENT NO. : 10,360,650 B2
APPLICATION NO. : 14/133685
DATED : July 23, 2019
INVENTOR(S) : Harris et al.

Page 1 of 1

It is certified that error appears in the above-identified patent and that said Letters Patent is hereby corrected as shown below:

On the Title Page

Item (73) Assignee:
Line 1  Delete "INNOVATION" and insert -- INNOVATIVE --, therefor.

In the Specification

Column 12:
Line 64  Delete "of"" and insert -- of." --, therefor.

Signed and Sealed this
Twenty-fifth Day of August, 2020

Andrei Iancu
*Director of the United States Patent and Trademark Office*